(12) United States Patent
Kobayashi et al.

(10) Patent No.: US 8,206,976 B2
(45) Date of Patent: Jun. 26, 2012

(54) CULTURE SYSTEM, CULTURE APPARATUS, CULTURE VESSEL BOX, AND AIR CLEANING METHOD

(75) Inventors: Toyoshige Kobayashi, Hatoyama (JP); Kazutoshi Kan, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 1394 days.

(21) Appl. No.: 11/756,015

(22) Filed: May 31, 2007

(65) Prior Publication Data
US 2007/0281351 A1    Dec. 6, 2007

(30) Foreign Application Priority Data

Jun. 2, 2006  (JP) ................................. 2006-154765

(51) Int. Cl.
*C12M 1/00* (2006.01)
*C12M 3/00* (2006.01)
*C12M 1/22* (2006.01)

(52) U.S. Cl. ............... 435/303.1; 435/289.1; 435/305.2; 435/305.3; 435/307.1; 435/809

(58) Field of Classification Search .... 435/283.1–309.4, 435/809
See application file for complete search history.

(56) References Cited

U.S. PATENT DOCUMENTS

| | | | | |
|---|---|---|---|---|
| 3,187,744 A | * | 6/1965 | Dorsak et al. | 600/22 |
| 4,495,892 A | * | 1/1985 | Jodar et al. | 119/482 |
| 6,228,635 B1 | * | 5/2001 | Armstrong et al. | 435/286.5 |
| 2001/0006812 A1 | * | 7/2001 | Tamaoki et al. | 435/303.1 |
| 2005/0084420 A1 | * | 4/2005 | Osawa et al. | 422/99 |
| 2006/0177922 A1 | * | 8/2006 | Shamah et al. | 435/286.2 |

FOREIGN PATENT DOCUMENTS

| | | |
|---|---|---|
| JP | 2001-039537 | 2/2001 |
| JP | 2002-262856 | 9/2002 |

\* cited by examiner

*Primary Examiner* — Nathan A Bowers
*Assistant Examiner* — Lydia Edwards
(74) *Attorney, Agent, or Firm* — Mattingly & Malur, PC (57) ABSTRACT

The present invention enables to keep the culture vessel clean with the clean air without touching the open air in which floating bacteria exist, and to culture cells with taking in and out the culture apparatus under the environment with low damages for the cells in constant temperature. The present invention is the culture vessel box which has one or more culture vessels, has the heater, and has the door outside which the good adhesive resin film is stuck, the culture apparatus which has various apparatuses including a heater and culture cells, and has the door outside which the resin film is stuck similarly to the culture vessel box and has its storing chamber. So, it is characterized in that the culture vessel box and the culture apparatus are connected with keeping an interior of the culture vessel box, including a culture vessel, and the interior of the culture apparatus in the clean state and constant temperature by sticking mutual doors of the culture vessel box and culture apparatus at the time of connection to confine the dirty portion which touched on open air by adhesiveness of their resin films, and moving the doors to the door storing chamber integrally.

22 Claims, 12 Drawing Sheets

CULTURE SYSTEM, CULTURE APPARATUS, CULTURE VESSEL BOX, AND AIR CLEANING METHOD

CLAIM OF PRIORITY

The present application claims priority from Japanese application JP 2006-154765 filed on Jun. 2, 2006, the content of which is hereby incorporated by reference into this application.

BACKGROUND OF THE INVENTION

1. Field of the Invention

The present invention is concerning culture system to culture cells, culture apparatus, culture vessel box, and air cleaning method. In particular, this is the contents about sterilely connect the processing chamber to the storing chamber to store processing objects in and those which enable to take out the object sterilely after processing.

2. Background Technology

Heretofore, the cell culture operation was done by skilled specialists in a clean room excluding bacteria as possible. Therefore, when culturing a lot of cells toward industrialization, they may arise increase of workers' loads, time and cost which are necessary for education and training of workers, artificial mistakes and mistaking samples, and contamination by those who hold bacteria. Then, we will need much costs for those measures. It becomes a large wall in industrialization.

Then, from the idea that automation of a culture progress can solve these problems, JP Patent Publication No. 2002-262856A discloses an example of an automatic cell culture. In the cell culture apparatus described in JP Patent Publication No. 2002-262856A, an apparatus to exchange culture medium automatically is equipped with an incubator, a robot exchanging culture medium, and a management computer. That takes out a cell culture tray from the inside of the incubator with a transfer robot, inserts new liquid medium with the needle after discharges old liquid medium in the culture tray with a needle, and stocks the culture tray into the incubator.

In addition, in a series of the progress culturing cells with an automatic apparatus, what is supplied into a clean interior of the culture apparatus from the external are mainly cells and culture vessels. It is necessary to supply one or more culture vessels to culture cells inside the culture apparatus into the interior of the culture apparatus with being kept the clean environment. Techniques related to this one are widely developed in delivery of wafers in semiconductor production, and it is thought the method of preventing dust from the external by double doors or air flow. For example, it is disclosed in JP Patent Publication No. 2001-39537A.

Nevertheless, techniques disclosed in JP Patent Publication No. 2002-262856A and JP Patent Publication No. 2001-39537A do not provide the best measure for solving important issues in cell culture. Thus, when culturing a cell, the contamination of cultured cells by dust, bacteria, and viruses which exist inside the air or with a human body poses a severest issue. So, it is the most important to control their quality. Therefore, we must carry out all steps generally called cell culture such as cell extraction, processing, and production under aseptic conditions, manipulate never to enter contaminants, and record its history.

For performing culture and processing of cells, it is necessary that the skillful technician who wears dustproof clothing works in the CPC (Cell Processing Center) which is certified in GMP (Good Manufacturing Practice) and is the large-scale culture institution given sterilization treatment in the whole facility. In industrialization, this has been a serious obstruction to productivity and cost. Then, the development of the automatic culture apparatus is demanded to develop the automatic culture apparatus which performs quality maintenance by performing the operation of the level equalled to a skilled technician in the environment where those who are the largest pollution sources are eliminated in processes as much as possible with automation technology, and performs cell culture with a culture vessel in high cleanliness.

In an interior of the culture apparatus, it is possible to shut off the interior from the external except supply of cells and culture vessels to keep the internal state clean, by providing an ultraviolet lamp as same as a clean bench and continuing to supply clean air through a HEPA filter and so on.

Then, it is necessary to put the culture vessel, which contacts the cells from the external in the culture apparatus with maintaining the cleanest state so that dust and bacteria may never enter into the interior. Moreover, it is necessary to take out the cells cultured inside the culture apparatus with maintaining the clean state inside the culture apparatus, then, to lessen the sharp temperature change, and to move it to an operating room or a processing facility keeping the same state.

The present invention was made in view of such the present circumstances, and provides the apparatus which can connect culture vessel and the interior of culture apparatus sterilely, can take out the sterile culture vessel after culturing the cells, and can achieve reduction of environmental stress such as temperature.

SUMMARY OF THE INVENTION

In order to solve the above-described issues, the present invention provides the culture vessel box which has a first slide door and stores one or more culture vessels. This culture vessel box can keep internal temperature and humidity constant, and can keep the environment clean by sending clean air into the interior of the culture vessel box to make the interior into positive pressure. Furthermore, it is possible to carry this box since a handle is attached. The culture apparatus is equipped with a second sliding door with a motor, a storing chamber of the door, and a mount for placing a culture vessel box, and a culture vessel box is placed in a predetermined position on the mount. At that time, such construction that the first slide door and the second slide door are stuck on the basis of guides provided in the doors is adopted, which makes it possible to have both slide doors slide integrally with confining dust and bacteria which exist in air by providing a resin material with good adhesiveness on each adhesive surface of both the first and second slide doors. Furthermore, it is enabled to exclude bacteria and dust even if they invade from the external through a gap or the like by controlling the air flow to evacuate the storing chamber of the moved slide doors with a fan at the time of connection, to make the storing chamber into negative pressure and make an interior of the culture apparatus and the culture vessel box into positive pressure. Thereby, it is possible to provide the apparatus which can deliver culture vessels in the clean environment where the open air does not enter and the environment with small temperature change.

That is, the culture system according to the present invention comprises a culture vessel box which has the containing section for containing at least one culture vessel, a first door section which enables to carry in and out the culture vessel, a culture apparatus which has sections for culturing cells internally, and a second door section which enables to carry in and out the culture vessel, and driving means for opening and closing the first and second door sections at the time of connection of the culture vessel box, characterized in that an open air contacting portion of at least one of the first and second door sections has adhesive raw material, and when the culture vessel box is connected to the culture apparatus, the first door section of the culture vessel box and the second door section of the culture apparatus stick with the adhesive raw material.

The culture apparatus according to the present invention to perform cell culture is comprised of the section to connect a culture vessel box which has the section for containing at least one culture vessel, a first door section which enables to carry in and out the culture vessel, the section to culture cells, a second door section which enables to carry in and out the culture vessel, and door drive means to open and close the first and second door sections at the time to connect the culture vessel box inside the culture apparatus. That is characterized in that an open air contacting portion of at least one of the first and second door sections has an adhesive raw material, and when the culture vessel box is connected to the culture apparatus, the first door section of the culture vessel box and the second door section of the culture apparatus stick with the adhesive raw material.

Furthermore, the culture vessel box according to the present invention to be connected to a culture apparatus for performing cell culture is comprised a vessel containing section for containing at least one culture vessel, a door section which enables to carry in and out the culture vessel, and a connecting section for connecting the culture vessel box to the culture apparatus. That is characterized in that an open air contacting portion of the door section has an adhesive raw material and, when the culture vessel box is connected to the culture apparatus, the door section of the culture vessel box and a door section of the culture apparatus stick with the adhesive raw material.

In addition, the air cleaning method according to the present invention is to keep air inside a storing chamber and a processing chamber clean when the storing chamber to store the processing object and the processing chamber for performing predetermined processing to the processing object are connected. So, that has at least one of open air contacting portions in doors of connecting sections of the storing chamber and the processing chamber having an adhesive raw material. That is characterized by a step of raising a door of the storing chamber and a door of the processing chamber integrally after the storing chamber is connected to the processing chamber, and a step of executing carrying-in/-out of the processing object after the doors of the storing chamber and the processing chamber are opened.

Furthermore, another culture system according to the present invention is characterized by comprising a culture vessel box which has a vessel containing section to contain at least one culture vessel, a first door section which enables to carry in and out the culture vessel, a culture apparatus which has a cell culture section to culture cells, a second door section which enables to carry in and out the culture vessel, connection detecting means of detecting that the culture vessel box and the culture apparatus are connected, means driving door for opening and closing the first and second door sections at the time to connect the culture vessel box, and means to control air flow of operating when the culture vessel box is connected.

Further features of the present invention will become apparent by the following Detailed Description of the Preferred Embodiments and accompanying drawings.

According to the culture system of the present invention, it is possible to connect a culture vessel and an interior of a culture apparatus sterilely and to take out the sterile culture vessel after culturing cells, and to achieve reduction of environmental stress, such as temperature.

DETAILED DESCRIPTION OF THE PREFERRED EMBODIMENTS

Figure 1:
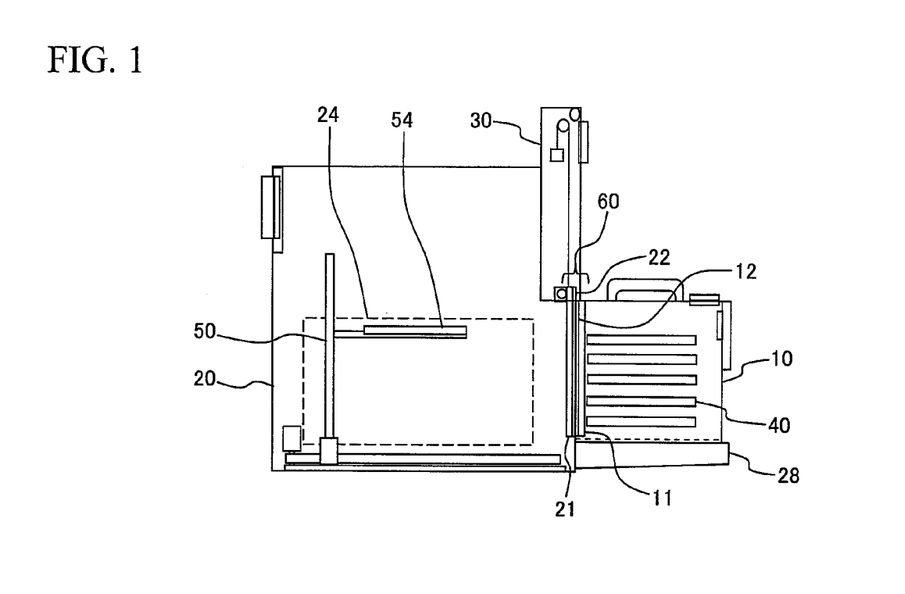
FIG. 1 is a general view of culture system to be constructed by connecting culture vessel box 10 to culture apparatus 20, according to the embodiment of the present invention.
Figure 4:
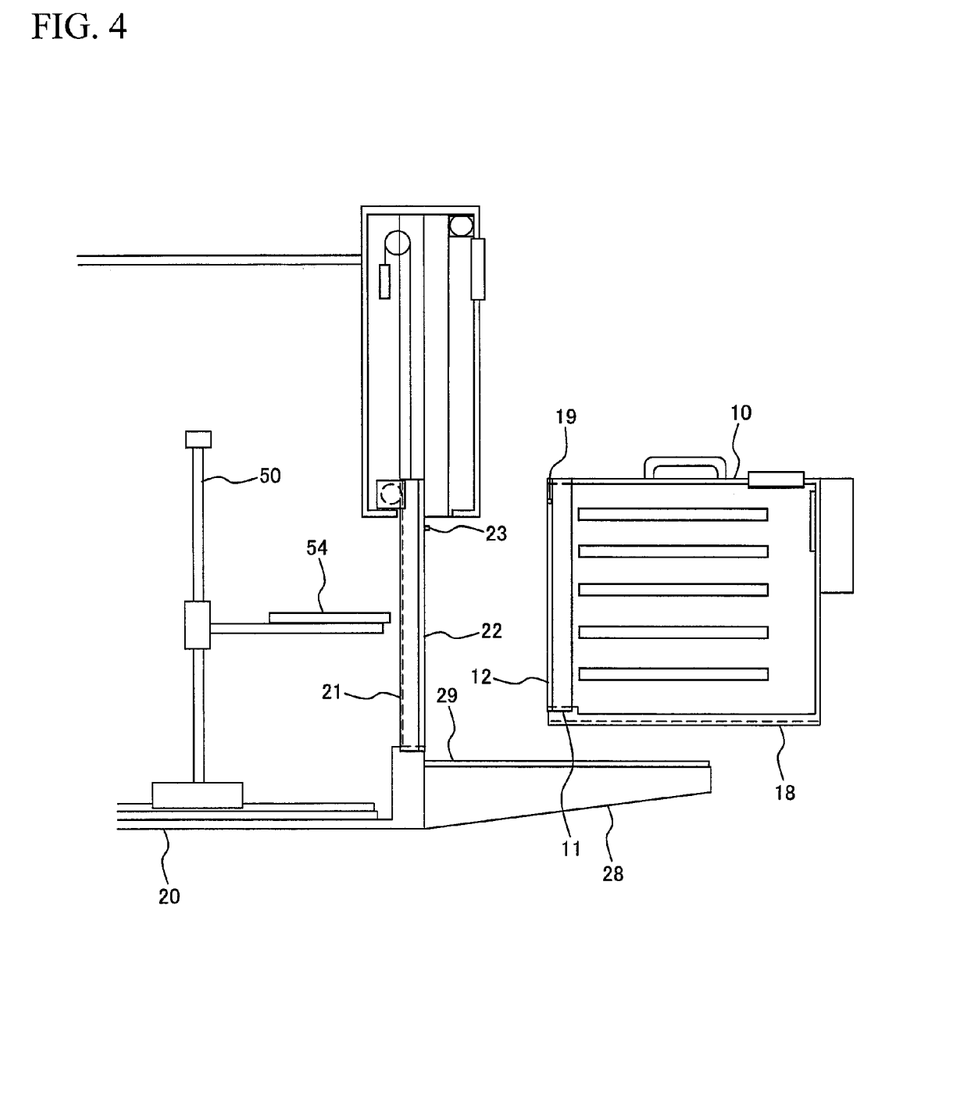
FIG. 4 is a conceptual diagram illustrating a state before connecting the culture apparatus 20 with the culture vessel box 10, about a culture system according to the embodiment of the present invention.
Figure 5:
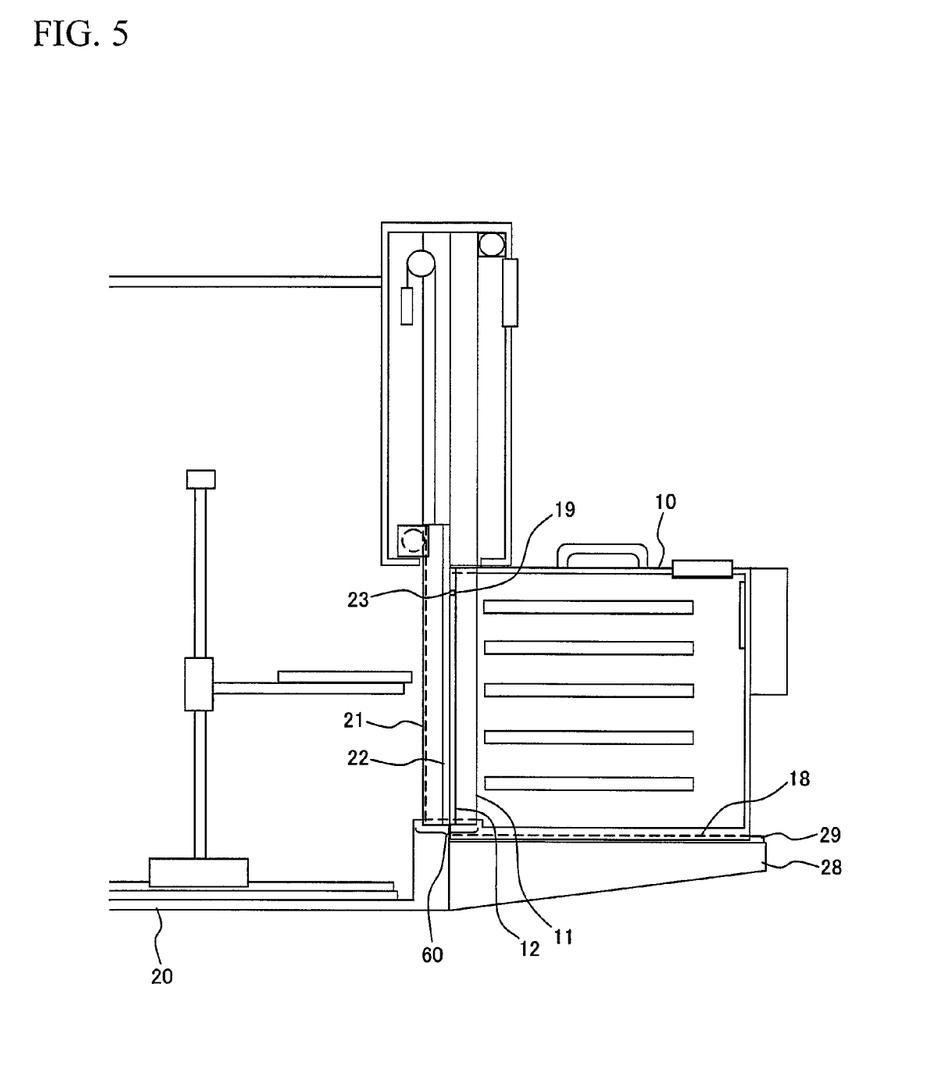
FIG. 5 is a conceptual diagram illustrating a state after connecting the culture apparatus 20 and culture vessel box 10, about a culture system in an embodiment of the present invention.
Figure 6:
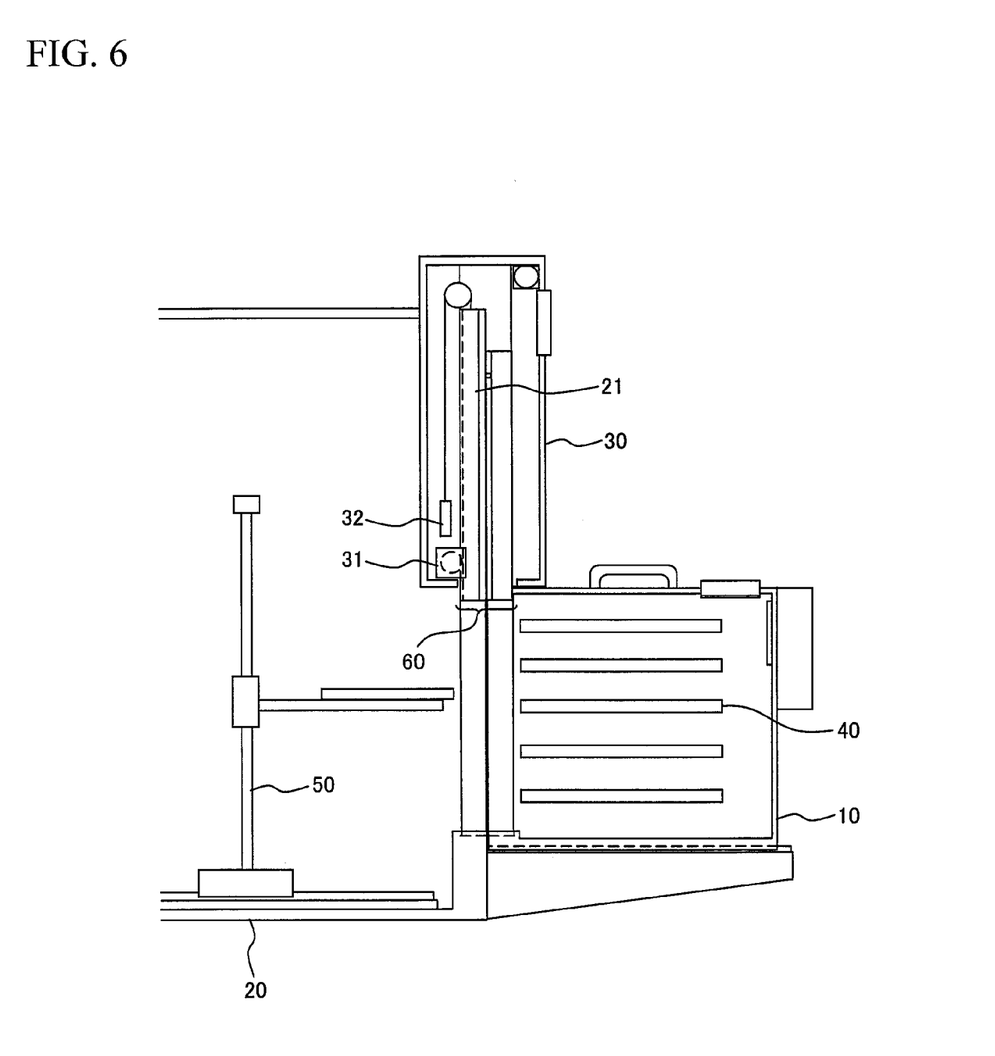
FIG. 6 is a conceptual diagram illustrating a state that two doors 60 (sticking culture vessel door 11 and apparatus door 21) are opened, about a culture system in an embodiment of the present invention.
Figure 7:
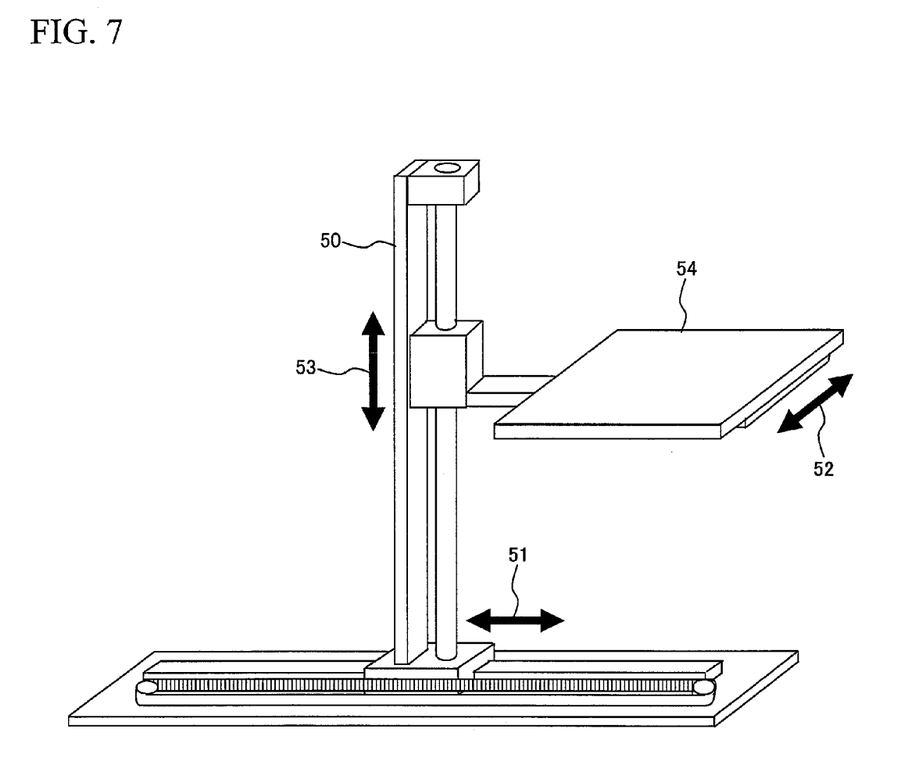
FIG. 7 is a structural diagram of the culture vessel manipulator 50 to move the culture vessel 40 in the culture apparatus 20.
Figure 8:
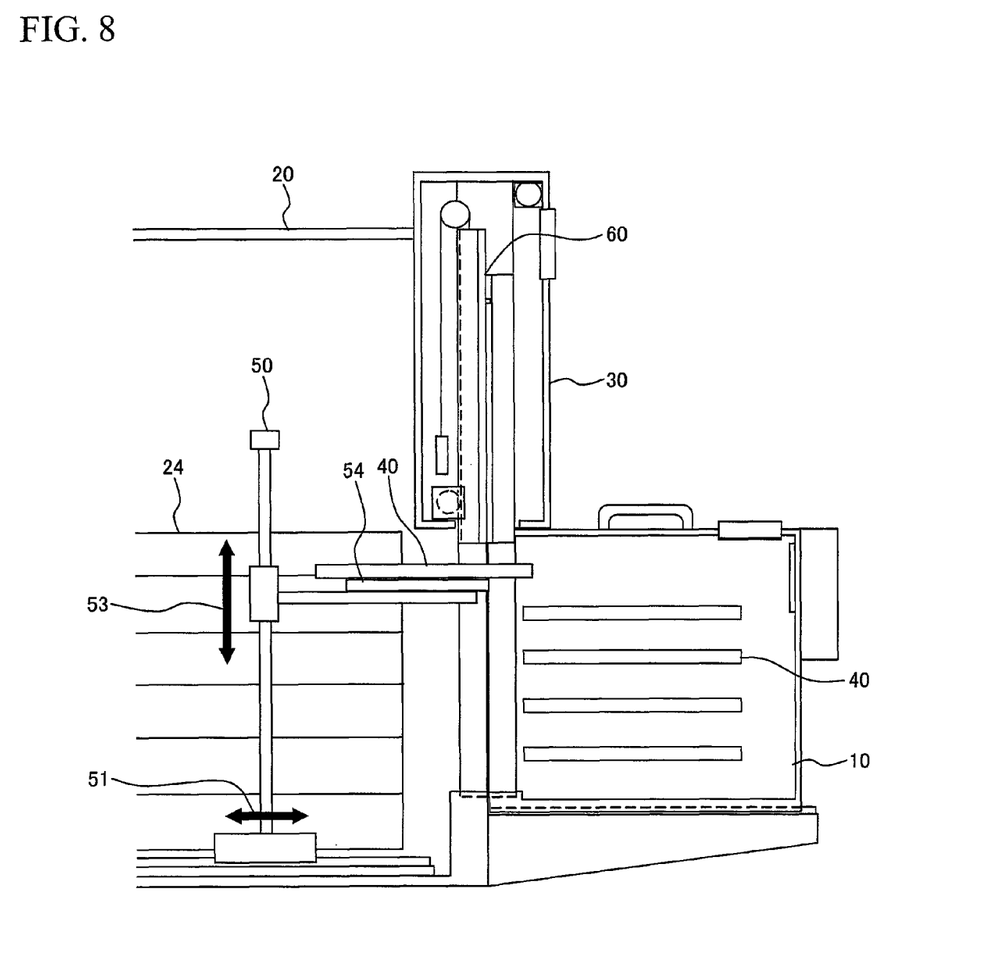
FIG. 8 is a conceptual diagram illustrating a state to move the culture vessel 40 with the culture vessel manipulator 50, about a culture system in an embodiment of the present invention.
Figure 9:
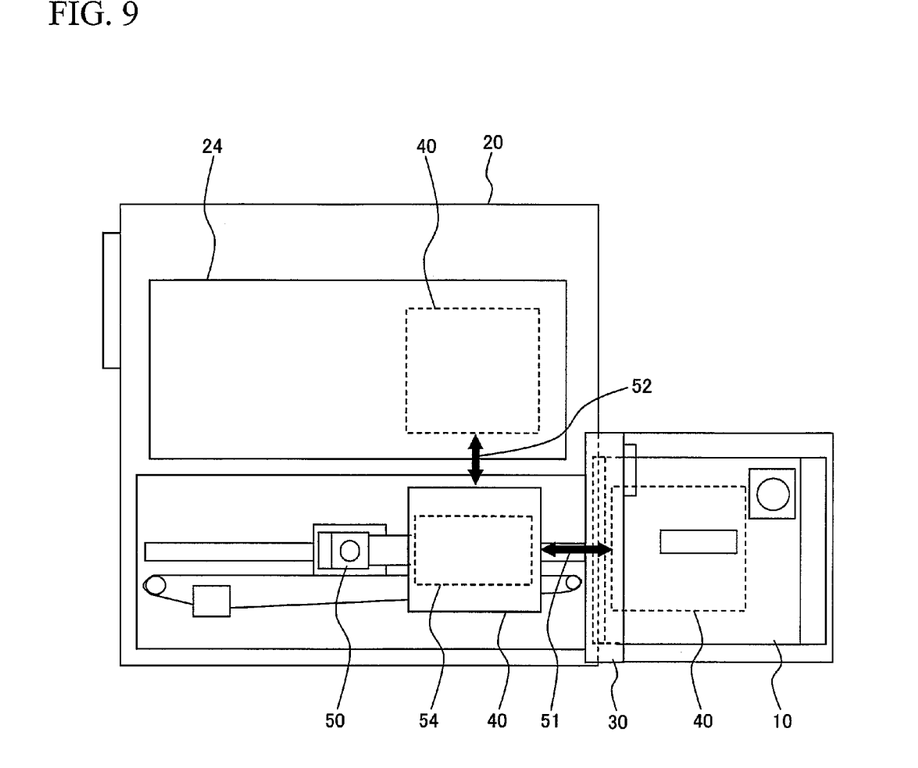
FIG. 9 is a top view illustrating a state to move the culture vessel 40 with the culture vessel manipulator 50, about a culture system in an embodiment of the present invention.
Figure 10:
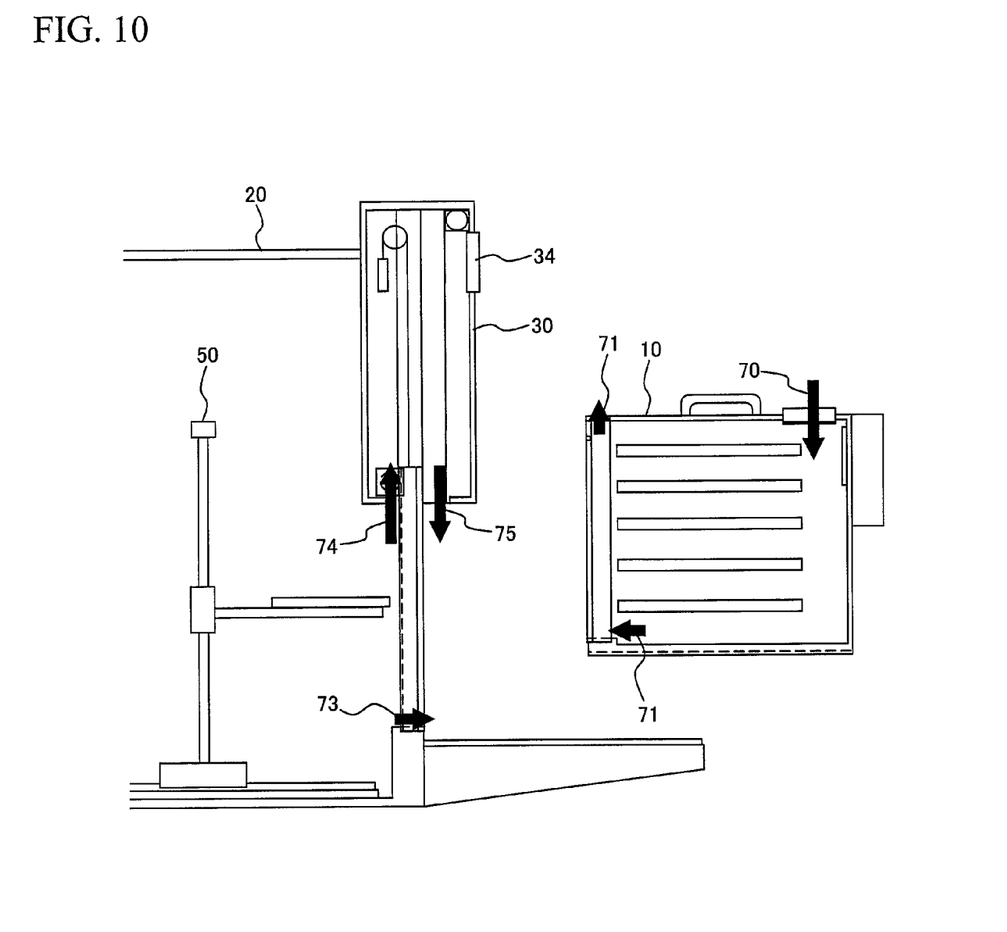
FIG. 10 is a conceptual diagram illustrating a state of each internal air flow in the culture vessel box 10 and culture apparatus 20 before connecting, about a culture system in an embodiment of the present invention.
Figure 11:
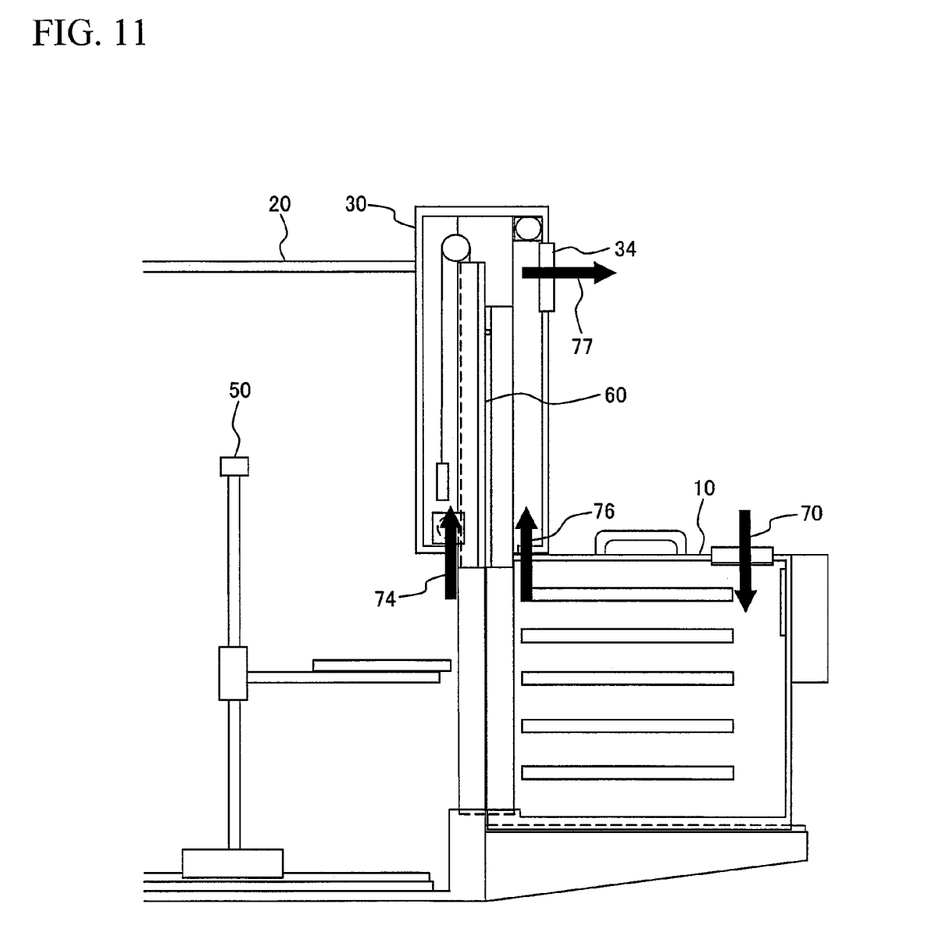
FIG. 11 is a conceptual diagram illustrating a state of an air flow inside the system after connecting the culture vessel box 10 to culture apparatus 20, about a culture system in an embodiment of the present invention.

Hereafter, embodiments of the present invention will be described with referring to drawings. FIG. 1 is a general view at the time to connect a culture vessel box 10 to a culture apparatus 20 which especially expresses features in the present invention, FIG. 2 is a structural diagram of the culture vessel box 10, FIG. 3 is a structural diagram of the culture apparatus 20, FIGS. 4 and 5 are schematic diagrams to connect the culture vessel box 10 to the culture apparatus 20, FIG. 6 is a schematic diagram to open and close a door of the culture vessel box 10 (hereafter, the vessel box door 11), and a culture apparatus door (hereafter, the apparatus door 21), FIG. 7 is a schematic diagram of the culture vessel manipulator 50, FIGS. 8 and 9 are schematic diagrams regarding movement of the culture vessel 40, and FIGS. 10 and 11 are diagrams regarding the internal air flow.

Figure 2:
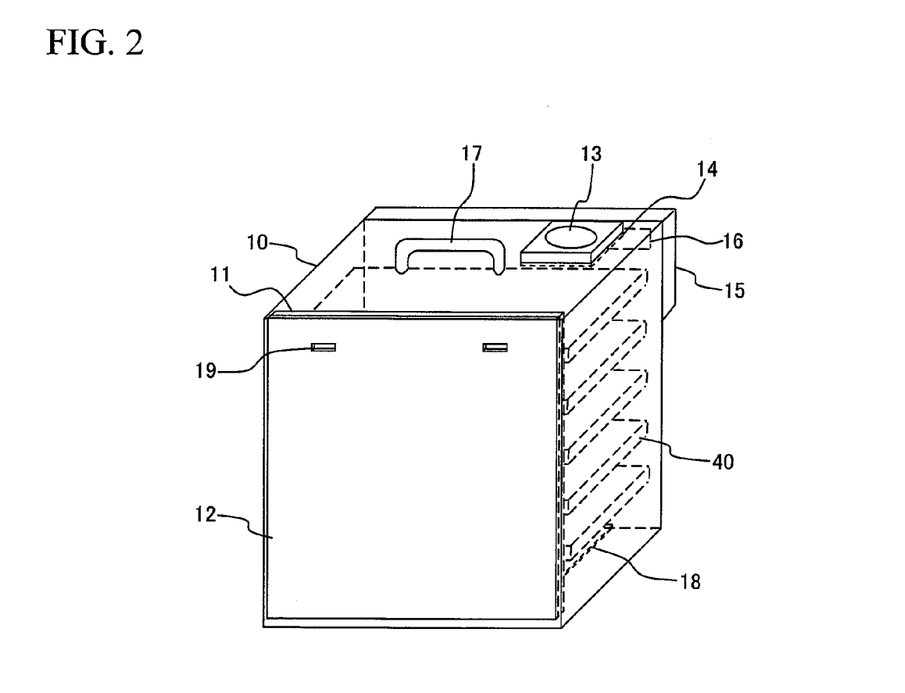
FIG. 2 is a diagram illustrating construction of the culture vessel box 10 which has one or more culture vessels inside and can be carried.
Figure 3:
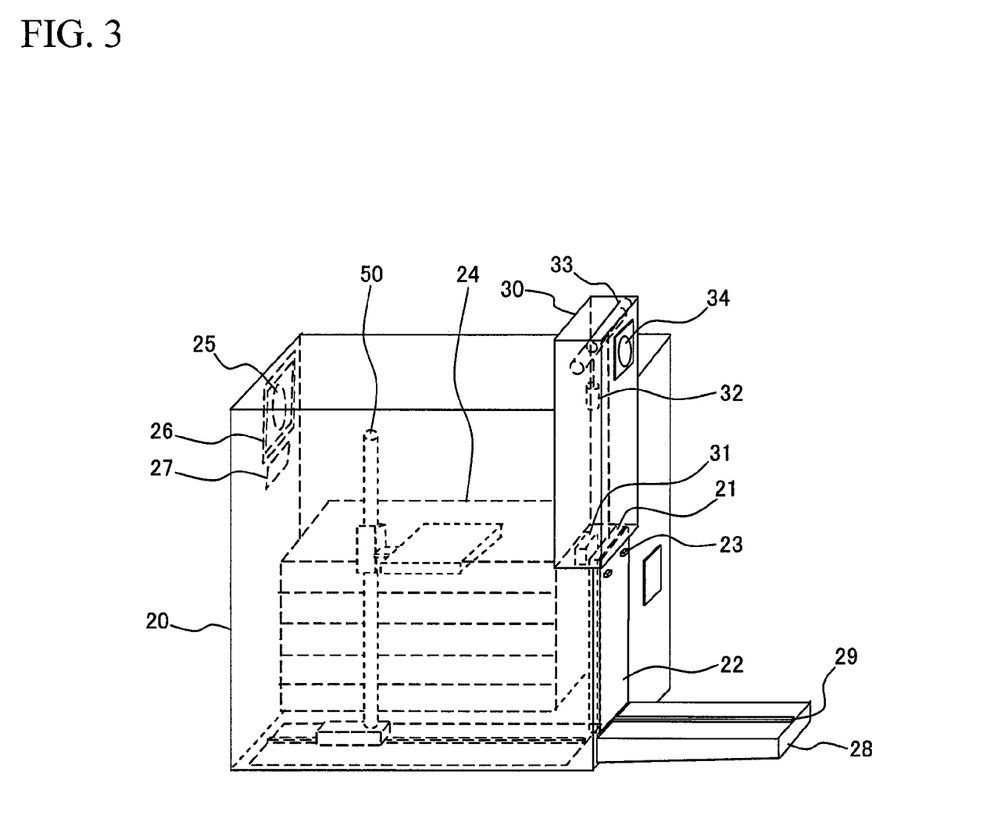
FIG. 3 is a diagram illustrating construction of the culture apparatus 20 which has culture chamber and culture vessel manipulator etc. and can perform a series of operations to culture cells.

In FIGS. 1, 2, and 3, we describe the construction of the culture vessel box 10 and the culture apparatus 20. Here, FIG. 1 is a side view at the time to connect the culture vessel box 10 in FIG. 2 to the culture apparatus 20 in FIG. 3 and join the vessel box door 11 to the apparatus door 21.

First, we describe the construction of the culture vessel box 10 in FIG. 2. One or more culture vessels 40 are storable in the interior of the culture vessel box 10. There is the vessel box door 11 to slid to one direction in a side of the culture vessel box 10, and it is possible to take in and out the culture vessel 40 to slid and open this door. A thin resin film 12 made from a resin material with good adhesiveness is stuck on the outside of the vessel box door 11, and it has the convexoconcave such as the claw receptacle 19. Furthermore, in order to make the interior of the culture vessel box 10 into positive pressure, the open air is blown into the interior by providing the fan 13 etc. in the culture vessel box 10. At that time, a filter 14 made of fine cellulose material such as HEPA filter is put into the front of a blowing opening of the fan 13 to prevent dust and bacteria etc. in the open air from entering into the interior of the culture vessel box 10. In order to make the fan 13 driven, the exchangeable battery 15 is installed in the culture vessel box 10. Since the open air is blown into the interior, temperature inside the culture vessel box 10 is dependent on the open air. So, we install thermoregulator 16 such as thermal storage material, Peltier device, or rubber heater in the interior. When using the thermoregulator 16, its electricity is supplied from the external battery 15 for the fan. Furthermore, the internal temperature change is lessened using insulation etc. on wall surfaces of the culture vessel box 10. In addition, it is possible to move the culture vessel box 10 easily by grasping the handle 17 installed in the culture vessel box 10. There is a trench 18 outside the bottom of the culture vessel box 10, and it is used for position fixation in the case of connection with the culture apparatus 20. In addition, when the guide 29 provided in the mount 28 of the culture apparatus 20 engages with this trench 18 as mentioned later, a position of the culture vessel box 10 is fixed.

We describe the construction of the culture apparatus 20 in FIG. 3. There are the culture chamber 24 and the culture vessel manipulator (hereafter, the manipulator 50) to handle the culture vessel 40 inside the culture apparatus 20. The culture chamber 24 keeps suitable for culturing the cells, to the environment in 37 degrees C., 5% of carbon dioxide concentration, and 100% of humidity. The cells is put into internal culture space of the culture vessel 40 and is cultured in the culture chamber 24, The manipulator 50 moves the culture vessel 40 to the interior of the culture vessel box 10, the culture chamber 24, and the test area and the area seeding cells and exchanging in the interior of the culture apparatus 20. In order to make the interior of the culture apparatus 20 into positive pressure, there are the filter 26 and the heater 27 for temperature control in the inside of the fan 25 similar to the fan 13 in the culture vessel box 10 to supply clean opening air to the interior. In the external of the culture apparatus 20, there is the mount 28 to install the culture vessel box 10, and there is the guide 29 to connect to the trench 18 in the bottom of the culture vessel box 10 to fix a position. The thin resin film 22 is stuck on the apparatus door 21 similarly to the vessel box door 11, and further, there is the claw 23 so as to make the claw receptacle 19 of the vessel box door 11 suitable in order to fix a position in the case of adhesion of the apparatus door 21 and the vessel box door 11. There is the door storing chamber 30 outside the culture apparatus 20, and this stores the sticking two doors 60 when the culture apparatus 20 is connected with the culture vessel box 10 and the vessel box door 11 and the apparatus door 21 are stuck and slided together. When making two doors 60 slide, the motor 31 installed in the apparatus door 21 is used, and the weight 32 to reduce load of the motor 31 is connected to the apparatus door 21. In addition, since the ultraviolet lamp 33 is included inside of this door storing chamber 30, it is possible to sterilize the interior to keep it clean. Furthermore, the exhaust fan 34 is installed in the door storing chamber 30, and it is used to perform exhaust 77 of internal air to the external at the time of connection.

In FIGS. 4 and 5, we describe to connect the culture vessel box 10 to the culture apparatus 20. In FIG. 4, we illustrate a state before connecting the culture vessel box 10 to the culture apparatus 20, and, in FIG. 5, illustrate a state of the sticking two doors 60 after connection of two doors.

In FIG. 4, the culture vessel box 10 is placed on the mount 28 which protrudes from an outside of the culture apparatus 20. The guide 29 is provided in the mount 28, a connecting position of the culture vessel box 10 and the culture apparatus 20 is fixed by aligning the trench 18 of the culture vessel box 10 with there, then, both of outer side faces of the vessel box door 11 and the apparatus door 21 are stuck, and, for the purpose to fix the connecting position of the adhesive surfaces, the claw receptacle 19 is installed in the vessel box door 11 and the claw 23 are installed in the apparatus door 21.

Furthermore, in FIG. 5, it is possible to improve cleanliness by enhancing adhesion of the vessel box door resin film 12 and the apparatus door resin film 22 which are provided in stuck faces to make it easy to slide together. Thus, since outsides of the vessel box door 11 and the apparatus door 21 are in contact with the open air, there is a high possibility of contacting with dust and bacteria. For this reason, since dust is confined in the interior at the time of adhesion of the doors by providing the vessel box door resin film 12 and the apparatus door resin film 22, it is possible to secure cleanliness of the two doors 60 before and after the united two doors 60 slide. Although adhesion between the vessel box door resin film 12 and the apparatus door resin film 22 is strong, they can be removed as Post-it®. So, it is easy to detach the culture vessel box 10 after the end of culture. Then, since the internal temperatures of the culture vessel box 10 and the culture apparatus 20 are controlled with the thermoregulator 16 and the heater 27 almost equality, the culture vessel 40 after connection is movable without a temperature change. Thereby, it is possible to eliminate temperature stress to the cell inside the culture vessel 40.

In addition, by providing gas and humidity controllers (not illustrated) in each interior of the culture vessel box 10 and the culture apparatus 20, after putting the culture vessel 40 into the culture vessel box 20 with keeping the cell's conditions after the end of culture, it enables to remove the culture apparatus 10 and move only the culture vessel box 20 with keeping a state of the cultured cell.

FIG. 6 is a diagram to describe open and close of the two doors 60 after connecting the culture vessel box 10 to the culture apparatus 20. The motor 31 connected to the culture apparatus door 21 makes the two doors 60 which are stuck and united open and close in sliding. At this time, the weight 32 is connected to the culture apparatus door 21 in order to reduce the load applied to the motor 31 to open and close in sliding. The slided two doors 60 enter into the door storing chamber 30, and the two doors 60 are moved to a position which enables to move the culture vessel 40 with the manipulator 50. In addition, about whether the two doors 60 have moved to the predetermined position, for example, a sensor to detect existence of the two doors 60 may be provided in at least either of the culture vessel box 10 or the culture apparatus 20, an operation of the motor 31 may be controlled, or a door stopper may be provided inside the door storing chamber 30 to stop the motor 31 when the two doors 60 contact the door stopper.

In this way, by making the two doors 60 stick, slide, open and close together, and move to the door storing chamber 30, it enables to detach and attach the interiors of the culture vessel box 10 and the culture apparatus 20 with keeping the clean situation. In addition to the effect of the above-mentioned adhesion, by making exteriors stick and move to the door storing chamber 30, it is possible to keep a high cleanliness of the connecting faces of the culture vessel box 10 and the culture apparatus 20. In addition, by keeping the temperatures in both the culture vessel box 10 and the culture apparatus 20 at the almost same time, it is possible to lessen the temperature change of the culture vessel 40 after connecting the culture vessel box 10 to the culture apparatus 20.

We describe the movement of the culture vessel 40 at the time of connection, using from FIGS. 7 to 9. In FIG. 7, a whole structural diagram of the manipulator 50 is illustrated. The manipulator 50 in the culture apparatus 20 has such construction that it can operate in three axes of to-and-fro movement 51, right and left movement 52, and vertical movement 53, and places the culture vessel 40 on the culture vessel mount 54 to move it. Thereby, the manipulator 50 moves the culture vessel 40 to the culture vessel box 10, the culture chamber 24, the test area, and the cell seeding and medium exchanging area. In FIG. 8, it is a side view of the connecting section, and, in FIG. 9, it is a top view near the connecting section.

In from FIGS. 7 to 9, by the to-and-fro movement 51 and the vertical movement 53, the manipulator 50 moves the culture vessel 40 placed on the culture vessel mount 54 to the interior of the culture apparatus 20. When putting the culture vessel 40 into the culture chamber 24, the manipulator 50 moves the culture vessel 40 by the right and left movement 52, and moves the culture vessel 40 into the interior of the culture chamber 24 by the vertical movement 53. By moving the culture vessel 40 from the interior of the culture vessel box 10 to various apparatuses inside the culture apparatus 20 and vice versa, it is possible to move the culture vessel 40 to the interior of the culture vessel box 10 from the various apparatuses inside the culture apparatus 20.

In FIGS. 10 and 11, we describe the movement of the air flow in each interior of the culture vessel box 10 and the culture apparatus 20 before and after connection. In FIG. 10, in the culture vessel box 10, the open air which enters from the fan 13 becomes clean open air 70 through the filter into the interior of the box. The interior is made into positive pressure and the air flow 71 is passed from the gap to the external of the vessel box door 11. In addition, also in the culture apparatus 20, the clean open air is flowed into the interior and it is made into positive pressure, So, the air flow 73 from the gap in the vicinity of the apparatus door 21, the air flow 74 passing through the door storing chamber 30 from the interior of the culture apparatus 20, and the air flow 75 from the door storing chamber 30 to the external are passed. Thereby, it is possible to circulate the clean air given temperature control, to make the interior into positive pressure to prevent the open air from entering into the interior, and to keep the interior in the clean state. In FIG. 11, when the culture vessel box 10 and the culture apparatus 20 are connected, the exhaust fan 34 inside the door storing chamber 30 is operated for the internal air flow to be controlled, and the air flow 75 from the interior of the culture apparatus 20 to the door storing chamber 30, and the air flow 76 from the culture vessel box 10 to the door storing chamber 30 are given exhaust 77 so that dust and bacteria of the two doors 60 which touch the open air may be given the exhaust 77 outside the culture apparatus 20. When the two doors 60 are closed and the culture vessel box 10 is detached, the exhaust fan 34 is stopped to achieve movement of the air flow in FIG. 10. In addition, although the exhaust fan 34 is provided in the culture apparatus 20 in this embodiment, it is not limited to this, and it may be provided in a culture vessel box 10 or it may be provided in both the culture vessel box 10 and the culture apparatus 20.

Thus, it is possible to connect the interior of the culture apparatus 20 to the interior of the culture vessel box 10 with keeping the clean environment without touching the open air, to take the culture vessel 40 in and out easily, and to move the culture vessel 40.

Figure 12:
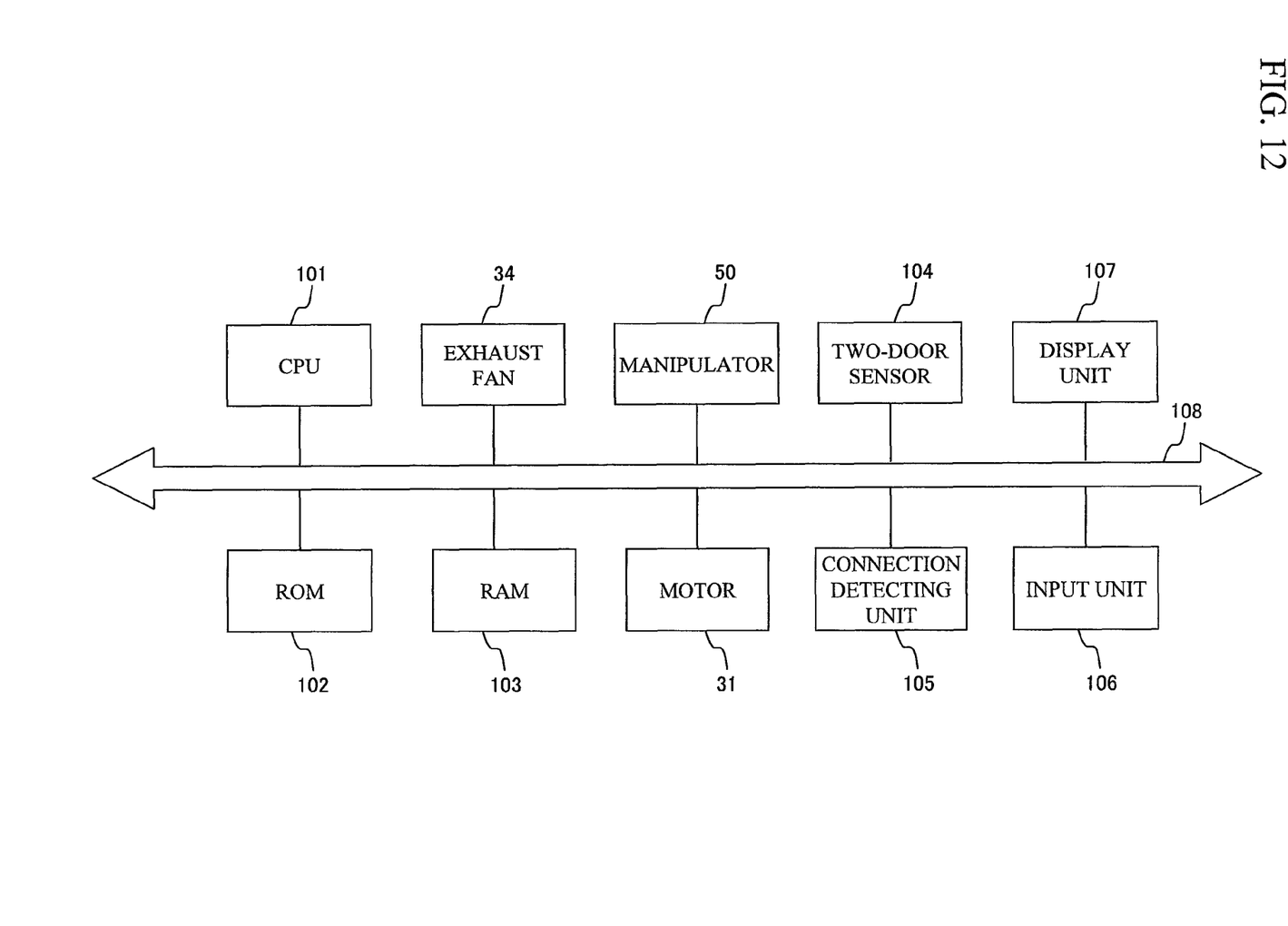
FIG. 12 is a block diagram illustrating a culture system in an embodiment of the present invention.
Figure 13:
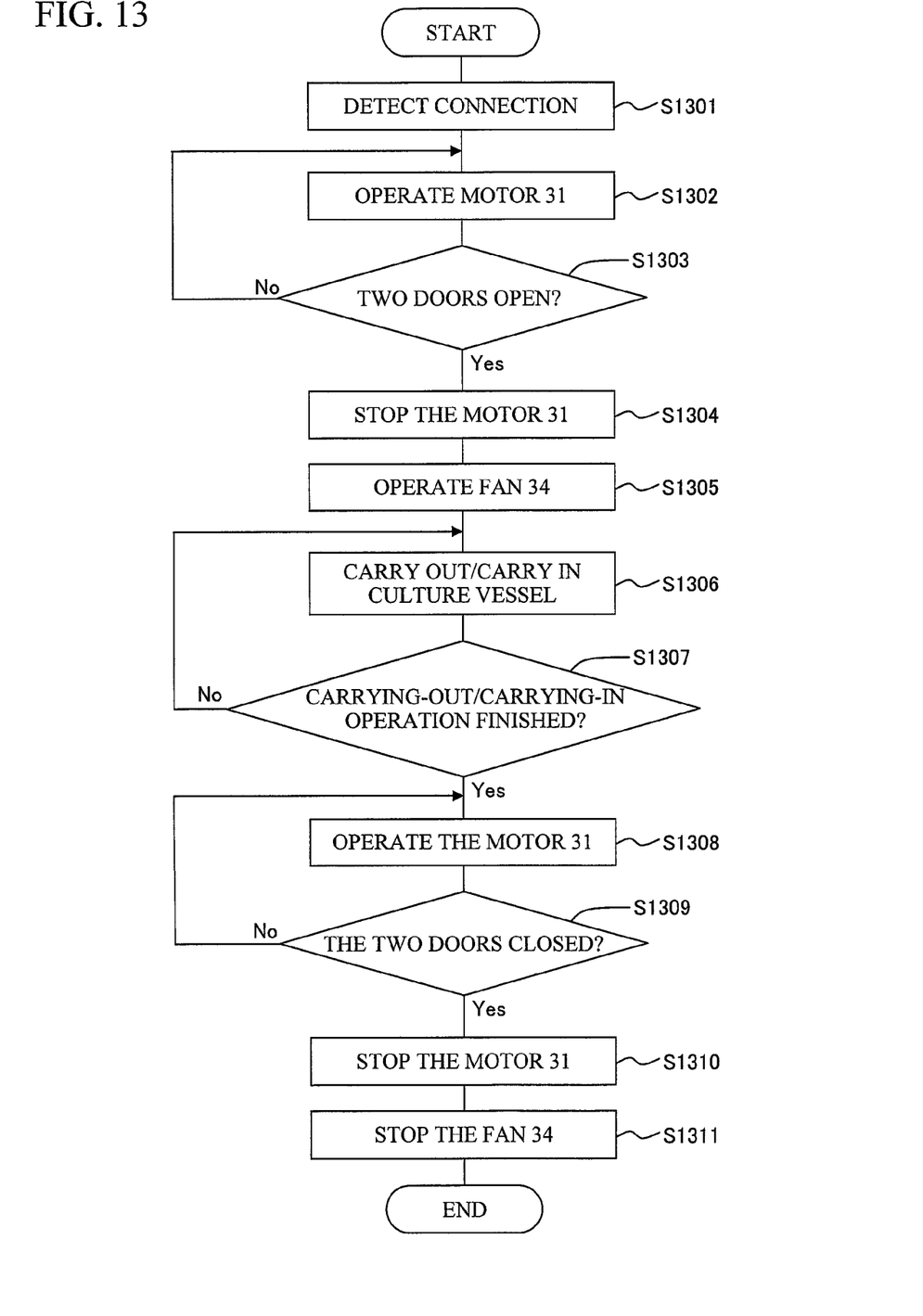
FIG. 13 is a flowchart to describe the operation of a culture system in an embodiment of the present invention.

In addition, the present invention enables to achieve the operations described above using a computer program. FIG. 12 is a block diagram illustrating the construction of portions relevant to computer control in the culture system (the culture vessel box 10 and the culture apparatus 20) according to the present invention. Since the exhaust fans 13 and 25 always operate and are not computer-controlled in order to make interiors into positive pressure, they are removed from FIG. 12. In addition, the bus 108 connects with each block in FIG. 12. FIG. 13 is a flowchart for describing an operation of the culture system.

In FIG. 12, the CPU 101 controls whole operations of the culture system and becomes at least a main control component of the operations in the flowchart illustrated in FIG. 13. Thus, the CPU 101 reads control programs which is based on the flowchart of FIG. 13 and is stored in ROM 102 at the time of the operation start of the system, develops it in RAM 103, and controls a whole system.

The exhaust fan 34 controls the air flow inside the system when the culture vessel box 10 is connected with the culture apparatus 20 as mentioned above. The motor 31 is driving means for making the two doors 60, which open and close the connecting portion of the culture vessel box 10 and the culture apparatus 20, rise and fall. The manipulator 50 carries in and out the culture vessel 40 at the time of opening of the two doors 60.

A two-door sensor 104 detects whether the two doors 60 open completely, and may be electric or mechanical as mentioned above. The connection detecting unit 105 detects whether the culture vessel box 10 is connected to the culture apparatus 20, and this may also be electric or mechanical.

The input unit 106 is, for example, for a user to instruct the carrying-in/-out of the culture vessel, and a keyboard and a mouse etc. correspond to this. The display unit 107 is, for example, for displaying that the culture system is working and instruction contents from a user etc., and CRT display and liquid crystal display etc. correspond to this.

Next, we describe operations of the culture system having the construction as shown in FIG. 12 using FIG. 13. In addition, the main operation unit is the CPU 101 unless otherwise specified.

When it is detected that the culture vessel box 10 is connected with the culture apparatus 20 (step S1301), the CPU 101 makes the motor 31 operate to raise the two doors 60 (step S1302). Then, it is judged whether the two doors 60 open completely (step S1303), and, if it completely opens, the processing will go to step S1304, and if it does not open completely yet, the processing will return to step S1302 and continue to operate the motor 31. As mentioned above, the opening of the two doors 60 is detected by the two-door sensor 104, and a detection result is transmitted to the CPU 101.

If it is determined that the two doors 60 open completely at step S1303, the operation of the motor 31 will be stopped (step S1304). In addition, if the culture vessel box 10 is connected with the culture apparatus 20, the fan 34 will start to operate and the air flow will be controlled by evacuating the air inside the culture system (step S1305).

When the two doors 60 open completely and the air flow inside the system is also regulated, the manipulator 50 is operated and carrying-in/-out processing of the culture vessel 40 is executed (step S1306). A user instructs whether the processing is carrying-in or carrying-out. Then, it is judged whether the carrying-out or carrying-in operation instructed by the user is completed (step S1307), and when it is completed, the manipulator 50 is stopped, the motor 31 is operated to start to close the two doors 60 (step S1308). Then, it is judged whether the two doors 60 are closed completely (step S1309), and when it is determined that it closed completely, the motor 31 is stopped (step S1310).

When it becomes in this state, the culture vessel box 10 can be detached. When detachment is detected, the operation of the fan 34 which controls the air flow is stopped (step S1311).

The carrying-in/-out operation of the culture vessel is executed as described above.

As described above, since the embodiment of the present invention can take in and out the culture vessel in the culture apparatus with eliminating contamination by dust as much as possible, and without cell stress by the temperature change with keeping cleanliness, and can carry the culture vessel after the end of culture as it is clean, it is expected that there are lot of needs and availabilities are much in industries, which requests high cleanliness, such as cell transplant and regenerative medicine.

This embodiment provides the culture vessel box which has the first slide door and can arrange and store one or more culture vessels. This culture vessel box can keep internal temperature and humidity constant, and can keep the environment clean by further sending clean air into the interior of the culture vessel box to make the interior into positive pressure. Furthermore, it is possible to carry or move this box since the handle etc. is attached. The culture apparatus is equipped with the second sliding door with the driving force, the storing chamber of the door, and a mount for placing the culture vessel box, and the culture vessel box is placed in the predetermined position on the mount. At that time, such construction that the first slide door and the second slide door are stuck on the basis of guides provided in the doors is adopted, which makes it possible to have both slide doors slide integrally with confining dust and bacteria in open air by adhesiveness to provide the resin material with good adhesiveness on each adhesive surface of both the first and second slide doors. Furthermore, it is enabled to exclude bacteria and dust even if they invade from the external through the gap by controlling the air flow by evacuating the storing chamber of the moved sliding doors with the fan at the time of connection, to make the storing chamber into negative pressure, and making the interior of the culture apparatus, and the culture vessel box into positive pressure. Thereby, it is possible to provide the apparatus which can deliver the culture vessel in the clean environment where the open air does not enter and the environment with small temperature change.

Then, according to this embodiment, it is possible not only to keep cleanliness to prevent dust or bacteria outside the slide door from entering into the interior by making sliding doors of the culture vessel box and the culture apparatus stick with the resin material with good adhesiveness in delivery of the culture vessel, but also to achieve space-saving by reducing drive systems, such as the motor, by opening the slide doors integrally. Furthermore, it is possible to easily perform attachment and detachment. Furthermore, it is possible to control an air flow in the connecting section of the culture vessel box and the culture apparatus by making the slide door storing space, which is the space to which the united sliding doors are moved, into negative pressure at the time of connection to make the interior of the culture apparatus and the culture vessel box into positive pressure, and to keep high cleanliness without entering the open air and portions, which touch the open air, into the interior.

In addition, the culture vessel is moved to the interior of the culture vessel box after the end of culture, and it is possible to carry the culture vessel with keeping cleanliness and temperature inside the culture vessel box, after closing the sliding door.

Furthermore, the present invention achieves the functions of the embodiment also with program code of software which achieves them. In this case, the memory medium which records the program code is provided to the system or the apparatus, and the computer (or CPU or MPU) of the system or the apparatus reads the program code stored in the memory media. In this case, since the program code itself read from the memory medium achieves the functions of the above-mentioned embodiments, the program code itself and the memory medium, recording it, construct the present invention. As such the memory medium for supplying the program code, for example, floppy™ disk, CD-ROM, DVD-ROM, hard disk, optical disk, magneto-optical disk, CD-R, magnetic tape, non-volatile memory card, or ROM is used.

Moreover, it is also sufficient that the OS (operating system) etc. which is working on computer executes some or all of actual processing on the basis of instructions of the program code, and the functions of the embodiment mentioned above is achieved by the processing. Furthermore, it is also sufficient that, after program code read from the memory medium is written in memory on the computer, the CPU etc. of the computer executes some or all of actual processing on the basis of instructions of the program code, and the functions of the embodiment mentioned above is achieved by the processing.

In addition, it is also sufficient that program code of software which achieves the functions of the embodiment is stored in memory means, such as hard disk or memory of the system or the apparatus, or the memory medium, such as CD-RW or CD-R by being distributed through the network, and the functions of the embodiment is achieved by the computer (or the CPU or the MPU) of the system or the apparatus reads and executes the program code stored in the memory means concerned or the memory medium concerned.

What is claimed is:

1. A culture system, comprising:
   a culture vessel box which has a vessel containing section to contain at least one culture vessel, and a first door section to carry in and out the culture vessel; and
   a culture apparatus which has a cell culture section for culturing cells internally, a second door section to carry in and out the culture vessel, door driving means for opening and closing the first and second door sections at the time of connection of the culture vessel box, and a door storing section which houses the first and second door sections therein when the first and second door sections are opened by the door driving means,
   wherein an open air contacting portion of at least one of the first and second door sections has an adhesive raw material,
   wherein when the culture vessel box is connected to the culture apparatus, the first door section of the culture vessel box and the second door section of the culture apparatus stick with the adhesive raw material, wherein the first and second door sections are housed within the door storing section when the first and second door sections are stuck to each other, and wherein the door storing section is provided outside a cell culturing space in the culture apparatus.

2. The culture system according to claim 1, wherein the door drive means moves the first and second door sections stuck to one another into the door storing section integrally.

3. The culture system according to claim 1, further comprising temperature control means to keep an interior of the culture vessel box and an interior of the culture apparatus in the same temperature.

4. The culture system according to claim 1, wherein each of the culture vessel box and the culture apparatus further comprises internal pressure control means for taking in open air to make an interior into positive pressure.

5. The culture system according to claim 4, wherein the internal pressure control means comprises a filter for preventing foreign material from open air from mixing.

6. The culture system according to claim 4, further comprising air flow control means which operates when the culture vessel box is connected to the culture apparatus, and controls an internal air flow.

7. A culture apparatus for performing cell culture, comprising:

a vessel containing section for containing at least one culture vessel, a connecting section to connect a culture vessel box having a first door section to carry in and out at least one culture vessel to/from the culture vessel box, a cell culture section for cell culture;

a second door section to carry in and out the culture vessel to/from the cell culture section; and door driving means for opening and closing the first and second door sections at the time of connection of the culture vessel box, wherein an open air contacting portion of at least one of the first and second door sections has an adhesive raw material, and a door storing section which houses the first and second door sections therein when the first and second door sections are opened by the door driving means, wherein the first door section of the culture vessel box and the second door section of the culture apparatus are stuck together with the adhesive raw material when the culture vessel box is connected to the culture apparatus, wherein the first and second door sections are housed within the door storing section when the first and second sections are stuck together, and wherein the door storing section is provided outside a cell culture space in the culture apparatus.

8. The culture apparatus according to claim 7, further comprising temperature control means for keeping temperature of an interior of the culture vessel box and temperature of an interior of the culture apparatus identically.

9. The culture apparatus according to claim 7, wherein each of the culture vessel box and the culture apparatus further comprises internal pressure control means for taking in open air to make an interior into positive pressure.

10. The culture apparatus according to claim 9, wherein the internal pressure control means comprises a filter for preventing foreign material from open air from mixing.

11. The culture apparatus according to claim 9, further comprising air flow control means to operate when the culture vessel box is connected to the culture apparatus, and to control an internal air flow.

12. A culture vessel box which is connected to a culture apparatus for performing cell culture, comprising:

a vessel containing section for containing at least one culture vessel;

a door section to carry in and out the culture vessel between the culture vessel box and the culture apparatus; and a connecting section for connecting the culture vessel box to the culture apparatus, wherein an open air contacting portion of the door section has an adhesive raw material, wherein the door section of the culture vessel box and a door section of the culture apparatus are stuck together with the adhesive raw material when the culture vessel box is connected to the culture apparatus, and wherein the door section of the culture vessel box and the door section of the culture apparatus are housed, when stuck together, within a door storing section which is provided outside a culture space in the culture apparatus.

13. The culture vessel box according to claim 12, further comprising internal pressure control means for taking in open air and making an interior into positive pressure.

14. The culture vessel box according to claim 12, further comprising temperature control means for keeping an interior of the culture vessel box at predetermined temperature.

15. An air cleaning method which keeps clean air inside a culture system, wherein the culture system includes a culture vessel box which has a vessel containing section to contain at least one culture vessel and a first door section to carry in and out the culture vessel; and a culture apparatus which has a cell culture section for culturing cells internally, a second door section to carry in and out the culture vessel, door driving means for opening and closing the first and second door sections at the time of connection of the culture vessel box to the culture apparatus, and a door storing section which houses the first and second door sections therein when the first and second door sections are opened by the door driving means, the method comprising:

a step of raising the first and second door sections integrally together after the culture vessel box is connected to the culture apparatus, to house the first and second door sections in the door storing section; and a step of executing carrying-in/-out of the culture vessel after the doors of the culture vessel box and the culture apparatus open, wherein at least one of open air contacting portions of the first and second door sections has an adhesive raw material and first and second door sections are integrally stuck together with the adhesive raw material at the time of connection of the culture vessel box to the culture apparatus.

16. The air cleaning method, according to claim 15, wherein at least one of the culture vessel box and the culture apparatus includes internal pressure control means for taking in open air and making an interior into positive pressure, the method further comprising a step of operating air flow control means which is provided in either one of the culture vessel box and the culture apparatus and which controls an internal air flow when the culture vessel box is connected to the culture apparatus.

17. The culture system according to claim 1, further comprising:
an air flow controller to control an internal air flow wherein the air flow controller operates when the culture vessel box is connected to the culture apparatus.

18. The culture system according to claim 1, further comprising temperature control means for keeping temperature of an interior of the culture vessel box and temperature of an interior of the culture apparatus identically.

19. The culture system according to claim 1, wherein at least one of the culture vessel box and the culture apparatus further comprises internal pressure control means for taking in open air to make an interior into positive pressure.

20. The culture system according to claim 1, wherein a height of the first door section is lower than a height of the second door section.

21. The culture system according to claim 11, wherein a height of the door section of the culture vessel box is lower than a height of the door section of the culture apparatus.

22. The culture system according to claim 1, wherein the door storing section internally includes an exhaust fan, and pressure inside the door storing section is set to negative pressure by the exhaust fan when the culture vessel box is connected to the culture apparatus.

* * * * *